United States Patent [19]

Dascalu et al.

[11] Patent Number: 6,075,017
[45] Date of Patent: *Jun. 13, 2000

[54] COMPOSITIONS FOR THE TREATMENT OF DANDRUFF

[75] Inventors: Avi Dascalu; Yoram Oron, both of Tel-Aviv, Israel

[73] Assignee: Ramot University Authority for Applied Research and Industrial Development Ltd., Ramat-Aviv, Israel

[ * ] Notice: This patent issued on a continued prosecution application filed under 37 CFR 1.53(d), and is subject to the twenty year patent term provisions of 35 U.S.C. 154(a)(2).

[21] Appl. No.: 08/913,650

[22] PCT Filed: Mar. 20, 1996

[86] PCT No.: PCT/US96/03988

§ 371 Date: Jan. 7, 1998

§ 102(e) Date: Jan. 7, 1998

[87] PCT Pub. No.: WO96/29045

PCT Pub. Date: Sep. 26, 1996

[30] Foreign Application Priority Data

Mar. 21, 1995 [IL] Israel ......................................... 113057

[51] Int. Cl.⁷ ..................... A61K 31/555; A61K 31/015; A61K 31/415

[52] U.S. Cl. .......................... 514/188; 514/764; 514/765; 514/396; 514/880; 514/881

[58] Field of Search ..................................... 514/396, 188, 514/764, 765, 880, 881; 421/702

[56] References Cited

U.S. PATENT DOCUMENTS

| | | | |
|---|---|---|---|
| 4,294,852 | 10/1981 | Wildnauer et al. | 424/317 |
| 4,491,588 | 1/1985 | Rosenburg et al. | 424/273 |
| 4,518,789 | 5/1985 | Yu et al. | 560/105 |

FOREIGN PATENT DOCUMENTS

93/07847   4/1993   WIPO .

OTHER PUBLICATIONS

CA 122: 248020, Cid, et al, Dec. 01, 1994.
CA 119: 15355, Mason et al, Apr. 29, 1993.
Blosis AN 91: 234987, McGrath, 1991.
CA 120: 212389, Wright et al, 1993.
Merck Index 10 edition, # 2374, # 6033, 1983.
Remingtons Pharmaceutical Sciences, p. 725, 1975.

*Primary Examiner*—Rebecca Cook
*Attorney, Agent, or Firm*—Ladas & Parry

[57] ABSTRACT

Seborrheic dermatitis of the scalp is treated by a synergistic combination of a cytotoxic agent and an antifungal agent.

15 Claims, No Drawings

COMPOSITIONS FOR THE TREATMENT OF DANDRUFF

This is a 371 of PCT/US96/03988 filed Mar. 20, 1996.

FIELD OF THE INVENTION

The invention relates to pharmaceutical compositions for use in the treatment of seborrheic dermatitis of the scalp.

BACKGROUND OF THE INVENTION

Dandruff, seborrheic dermatitis of the scalp, is a common disease involving 3–5% of the population. Dandruff is, in many cases, the precursor of alopecia (baldness) and constitutes a chronic and almost intractable cosmetical and social inconvenience. The pathophysiology of the disease remains unknown, although it is known to involve a hyperproliferative state of the skin, a limited inflammatory process, and a secondary microbial colonization by the lipophilic yeast Pityrosporum, which is abundant and significantly overpopulated on the scalp of seborrheic patients.

Dandruff is a chronic and almost incurable disease. Available treatments result only in short term effects with an eventual recurrence of the disease.

A traditional treatment of dandruff included administration onto the scalp of either a cytotoxic agent or an antifungal agent. However, as pointed out heretofore no treatment provides long term alleviation from the symptoms of this disease.

It is an object of the invention to provide a composition useful in the treatment of dandruff or symptoms associated therewith.

It is another object of the invention to provide a method for alleviation of dandruff or symptoms associated therewith.

GENERAL DESCRIPTION OF THE INVENTION

The present invention provides by a first of its aspects a composition, e.g. in the form of a hair shampoo, for the treatment of dandruff or of symptoms associated therewith, comprising in combination an effective amount of at least one cytotoxic agent and an effective amount of at least one antifungal agent, together with a carrier, a diluent or an excipient.

The term "effective amount" as used herein means to denote an amount of an agent effective in achieving a therapeutic result in the treatment of dandruff, such as alleviation of itching, a decrease in the amount of scales, a reduction in the rate of hair loss, a reduction in scalp redness, etc.

The term "cytotoxic agent" as used herein means to denote an agent which inhibits proliferation of keratinocytes skin cells. The term "antifungal agent" will be used to denote an agent which is specifically active in inhibiting growth of fungus and the fungus' ability to colonize the skin, which includes, intei alia, agents which are destructive to fungi, or active in suppressing growth of fungus or affect their ability to reproduce.

It will be appreciated by the artisan that the agents which are cytotoxic may also have some anti-fungal activity and an anti-fungal agent may also have some cytotoxic activity. Thus, the term "cytotoxic agent" refers to agents which are known in the art primarily by having cytotoxic activity and the term "antifungal agent" refers to agents which are known in the art primarily by their antifungal activity.

In the following description reference will at times be made to concentrations given in percent (%), this indication meaning the number of weight units of any ingredient in hundred weight units of an entire composition.

Examples of cytotoxic agents useful in accordance with the invention are coal tars, zinc pyrithione or the like. The preferred cytoxic agent is coal tar, typically included in the composition in concentration of 1–5%.

Examples of antifungal agents useful in accordance with the invention include imidazoles, ciclopiroxolamines and metronidazoles. The imidazoles, which are preferred in accordance with the invention, include ketoconozole, bifonazole, itraconazole, econazole, clotrimazole, miconazole, oxiconazole, isoconazole and the like. From the imidazoles, ketoconozole is particularly preferred. Typically, the antifungal agent is included in the composition in a concentration of 0.5–5%.

The present invention further provides the use of said cytotoxic agent in combination with said antifungal agent for the preparation of a composition, e.g. a medical hair shampoo, for the treatment of dandruff.

A further aspect of the invention is concerned with the treatment of individuals suffering from dandruff by combined application to the scalp of such individuals of said cytotoxic agent and of said antifungal agent. The individuals may be treated by the use of a single composition, e.g. in the form of a hair shampoo, comprising both agents. Alternatively, the individuals may be treated by a combination of two different compositions, one comprising said cytotoxic agent and the other said antifungal agent.

The above described combination may be applied 3–4 times during the first week from the start of the treatment, and 1–2 times a week, thereafter.

The present invention also pertains to a package comprising at least two compositions, one comprising said antifungal agent and the other said cytotoxic agent, optionally with instructions for use in said method.

In the following the invention will be illustrated with reference to a non-limiting specific embodiment described in the Example below.

EXAMPLE 1

A group of six patients (ages 17–38) with a severe case of dandruff were on a regular bi-weekly anti seborrheic treatment prior to the onset of the experiment. During the experiment they were treated with a combination of the following two compositions:

a. a composition comprising 1.8% coal tar b. a solution comprising 2% ketoconazole.

The patients were instructed to apply the two compositions, one after the other, in an amount sufficient to cover the entire scalp. The patients were instructed to apply the compositions on days 1, 3, 6 and 9. The patients' conditions were examined after 14 or 30 days following the onset of treatment.

The patients' conditions were evaluated by the following criteria:

(i) scaling—existence of scales on the scalp, typically at the temporal area;

(ii) itching—based on the patient's subjective feeling;

(iii) severity—overall assessment of the dandruff disease situation, taking into account the skin redness as an indication of inflammatory conditions.

For the above criteria a score was given by using the following scale:

0—non existing
1—minimal
2—moderate
3—severe

The results are shown in the following Table 1:

TABLE 1

| Patient |     |     | Scale |     | Itch |     | Severity |     |       |
| No.     | Age | Sex | B*    | A+  | B*   | A+  | B*       | A+  | Day   |
| 1       | 22  | m   | 2     | 0   | 2    | 0   | 2        | 0   | 30    |
| 2       | 38  | m   | 3     | 1   | 3    | 0   | 3        | 1   | 14    |
| 3       | 23  | m   | 2     | 0   | 2    | 0   | 2        | 0   | 14    |
| 4       | 27  | m   | 2     | 0   | 2    | 0   | 2        | 0   | 14    |
| 5       | 17  | f   | 3     | 1   | 3    | 1   | 3        | 1   | 14    |
| 6       | 37  | m   | 2     | 0   | 2    | 0   | 2        | 0   | 14,30 |

*B - before treatment according to the present invention;
+A - after treatment.

The results of Table 1 showt clearly that following treatment, there is a considerable decrease in scale formation, reduction in scalp redness and itching in all treated patients. The subjects reported that the improvements started within about five days from the onset of the treatment. Furthermore, this combined treatment brought to a remission of the disease's symptoms for about two weeks in some of the patients, after the treatment was terminated, as can be seen in the patients tested after thirty days.

EXAMPLE 2

A group of three patients who had no record of treatment for dandruff prior to the onset of the experiment, was given the same treatment as in Example 1. The patients' condition was as severe as in Example 1.

The results are shown in the following Table 2:

TABLE 2

| Patient |     |     | Scale |     | Itch |     | Severity |     |     |
| No.     | Age | Sex | B*    | A+  | B*   | A+  | B*       | A+  | Day |
| 1       | 32  | f   | 1     | 0   | 1    | 0   | 1        | 0   | 30  |
| 2       | 27  | f   | 2     | 1   | 3    | 1   | 2        | 1   | 30  |
| 3       | 24  | f   | 1     | 0   | 1    | 0   | 1        | 0   | 14  |

*B - before treatment according to the present invention;
+A - after treatment.

Again it is clearly demonstrated that the combined application of the two compositions, results in a substantial disappearance of the symptoms accompanying dandruff disease.

What is claimed is:

1. A composition for topical treatment of seborrheic dermatitis of the scalp comprising at least one cytotoxic agent and at least on antifungal agent in respective amounts sufficient to achieve a synergistic result in said treatment, said composition further comprising a carrier, a diluent or an excipient.

2. The composition according to claim 1 wherein the cytotoxic agent is selected from the group consisting of coal tar and zinc pyrithione, and the antifungal agent is an antifungal imidazole.

3. The composition according to claim 2, wherein the antifungal agent is selected from the group consisting of ketoconazole and bifonazole.

4. The composition according to claim 3, wherein the cytotoxic agent is coal tar.

5. The composition according to claim 1, wherein the cytotoxic agent is zinc pyrithione and the antifungal agent is ketoconazole.

6. The composition according to claim 1, wherein the cytotoxic agent is selected from the group consisting of coal tar and zinc pyrithione.

7. The composition according to claim 6, comprising 1 to 5% of said cytotoxic agent.

8. The composition according to claim 6, wherein the antifungal agent is selected from the group consisting of imidazoles and ciclopiroxolamines.

9. The composition according to claim 8, wherein the antifungal agent is selected from the group consisting of ketoconazole, bifonazole, itraconazole, econazole, clotrimazole, miconazole, oxiconazole and isoconazole.

10. The composition according to claim 8, comprising 0.5 to 5% of said antifungal agent.

11. A method for treatment of seborrheic dermatitis of the scalp of a user comprising applying to the scalp at least one cytotoxic agent in combination with at least one antifungal agent in respective amounts sufficient to achieve a synergistic result in said treatment.

12. The method according to claim 11, wherein the cytotoxic agent is selected from the group consisting of coal tar and zinc pyrithione, and the antifungal agent is an antifungal imidazole.

13. The method according to claim 12, wherein the antifungal agent is selected from the group consisting of ketoconazole and bifonazole.

14. The method according to claim 13, wherein the cytotoxic agent is coal tar.

15. The method according to claim 12, wherein the cytotoxic agent is zinc pyrithione and the antifungal agent is ketoconazole.

* * * * *